(12) United States Patent
Xu et al.

(10) Patent No.: US 12,055,513 B2
(45) Date of Patent: Aug. 6, 2024

(54) METHOD FOR PREPARING IMMUNOELECTRODE SYSTEM

(71) Applicant: LANSION BIOTECHNOLOGY CO., LTD., Jiangsu (CN)

(72) Inventors: Xingshang Xu, Jiangsu (CN); Jeffery Chen, Jiangsu (CN)

(73) Assignee: LANSION BIOTECHNOLOGY CO., LTD., Jiangsu (CN)

( * ) Notice: Subject to any disclaimer, the term of this patent is extended or adjusted under 35 U.S.C. 154(b) by 253 days.

(21) Appl. No.: 17/773,045

(22) PCT Filed: Dec. 29, 2020

(86) PCT No.: PCT/CN2020/140515
§ 371 (c)(1),
(2) Date: Apr. 29, 2022

(87) PCT Pub. No.: WO2021/115491
PCT Pub. Date: Jun. 17, 2021

(65) Prior Publication Data
US 2022/0390408 A1 Dec. 8, 2022

(30) Foreign Application Priority Data
Dec. 14, 2019 (CN) .......................... 201911289526.5

(51) Int. Cl.
*G01N 27/327* (2006.01)
*B01L 3/00* (2006.01)
(Continued)

(52) U.S. Cl.
CPC .... *G01N 27/3276* (2013.01); *B01L 3/502707* (2013.01); *G01N 27/3275* (2013.01);
(Continued)

(58) Field of Classification Search
CPC .................... G01N 33/5438; B01L 2300/0645
See application file for complete search history.

(56) References Cited

U.S. PATENT DOCUMENTS 6,652,720 B1 * 11/2003 Mansouri ........... G01N 27/3271
204/415
9,568,444 B2 * 2/2017 Wu ..................... G01N 33/5438
(Continued)

FOREIGN PATENT DOCUMENTS

CN        2662241 Y * 12/2004
CN      101655473     2/2010
(Continued)

OTHER PUBLICATIONS

English translation of CN2662241 (Year: 2004).*
(Continued)

*Primary Examiner* — Scott W Dodds
(74) *Attorney, Agent, or Firm* — JCIPRNET (57) ABSTRACT

Provided is a preparation method for an immunoelectrode. The immunoelectrode comprises a substrate, a gold layer, a conductive polymer layer and an antibody layer. The substrate, the gold layer, the conductive polymer layer and the antibody layer are sequentially attached from bottom to top. The preparation method for the immunoelectrode specifically comprises the following steps: (1) preparing the conductive polymer layer: preparing a polypyrrole layer on a gold-plated substrate to obtain a polypyrrole/gold-plated substrate; (2) preparing the immunoelectrode: preparing the antibody layer on the polypyrrole layer to obtain an antibody/polypyrrole/gold-plated substrate; and (3) forming an immunoelectrode system: fixing a bare gold-plated substrate to the outer side of the antibody/polypyrrole/gold-plated substrate to obtain the immunoelectrode system. A polypyrrole material is used for fixing an antibody of a biological
(Continued)

recognition element and immobilizing the antibody on the immunoelectrode.

12 Claims, 5 Drawing Sheets

(51) Int. Cl.
*G01N 33/543* (2006.01)
*G01N 33/547* (2006.01)

(52) U.S. Cl.
CPC ..... *G01N 27/3277* (2013.01); *G01N 27/3278* (2013.01); *G01N 33/5438* (2013.01); *G01N 33/547* (2013.01); *B01L 2300/0645* (2013.01)

(56) References Cited

U.S. PATENT DOCUMENTS

| | | | |
|---|---|---|---|
| 2003/0062263 | A1 | 4/2003 | Stanford et al. |
| 2006/0160164 | A1* | 7/2006 | Miller ................ G01N 33/5438 435/7.93 |
| 2008/0297169 | A1 | 12/2008 | Greenquist et al. |
| 2009/0117574 | A1* | 5/2009 | Labgold ................ C12Q 1/6825 435/7.1 |
| 2012/0190040 | A1* | 7/2012 | Talebpour ......... B01L 3/502715 435/7.1 |
| 2017/0173578 | A1 | 6/2017 | Crooks |
| 2017/0248591 | A1* | 8/2017 | Shinobu ........... G01N 33/54373 |

FOREIGN PATENT DOCUMENTS

| | | |
|---|---|---|
| CN | 102680683 | 9/2012 |
| CN | 108593719 | 9/2018 |
| CN | 108745429 | 11/2018 |
| CN | 109155441 | 1/2019 |
| CN | 109682878 | 4/2019 |
| CN | 111351931 | 6/2020 |
| CN | 211463197 | 9/2020 |
| CN | 111729696 | 10/2020 |
| JP | 2004028889 A * | 1/2004 |

OTHER PUBLICATIONS

English translation of JP2004-28889 (Year: 2004).*
Noel Nesakumar; et al., "Microfluidic Electrochemical Devices for Biosensing," Journal of Analysis and Testing, vol. 3, No. 1, Feb. 2019, pp. 3-18.
Archana Sahay; et al., "Synthesis and Characterization of Poly (p-phenylenediamine) in the Presence of Sodium Dodecyl Sulfate," Research Journal of Chemical Sciences, vol. 4, No. 2, Feb. 2014, pp. 60-67.
"International Search Report (Form PCT/ISA/210) of PCT/CN2020/140515," mailed on Mar. 30, 2021, with English translation thereof, pp. 1-6.

* cited by examiner

METHOD FOR PREPARING IMMUNOELECTRODE SYSTEM

CROSS-REFERENCE TO RELATED APPLICATION

This application is a 371 of international application of PCT application serial no. PCT/CN2020/140515, filed on Dec. 29, 2020, which claims the priority benefit of China application no. 201911289526.5, filed on Dec. 14, 2019. The entirety of each of the above mentioned patent applications is hereby incorporated by reference herein and made a part of this specification.

TECHNICAL FIELD

The present invention belongs to the field of electrochemical immunoassay, and in particular to a method for preparing an immunoelectrode.

DESCRIPTION OF RELATED ART

An electrochemical immunosensor is an analytical means based on specific binding of an antigen and an antibody, and has the advantages of fast detection, low detection limit, high sensitivity, easy operation and low preparation cost.

In recent years, electrochemical immunosensors have attracted much attention and are widely applied to the detection of tumor markers. When an immunosensor is used for continuous target detection, the regeneration property of a biomolecular probe is a major issue restraining the practical use of this type of sensors. Therefore, to develop an immunosensor that allows mass production and has a low cost as a disposable sensor will overcome the shortcomings such as tedious operations and waste of time and labor caused by regeneration treatment on a biomolecular probe needed during repeated measurements by an immunosensor. In the face of increasing special detection environments, it has become a development trend to develop novel sensor technologies based on new materials and new processes. A flexible sensor based on a flexible substrate material has the characteristics of flexibility, ductility, free bending and even folding, convenience in carrying, wearability and the like; and with diverse structural forms, it be placed at will according to the requirements of measurement conditions, and is applicable to many special application scenarios and environments. Common flexible materials include polyvinyl alcohol (PVA), polyester (PET), polyimide (PI), polyethylene naphthalate (PEN), paper sheets, textile materials, etc. For example, Xia Shanhong's research group at the Institute of Electronics, Chinese Academy of Sciences, develops a flexible immunosensor of a paper-based material, where a glycated hemoglobin detection immunosensor is achieved by self-assembling a single-layer film on a paper base and introducing gold nanoparticles; and Xu Panju from Zhejiang University of Technology prepares a sensor based on a graphene oxide (GO)/reduced graphene oxide (rGO) microarray on a flexible substrate (ITO/PET), which is used for providing a cell growth substrate and for sensitive detection of hydrogen peroxide.

A Chinese patent document (application No.: 201810668237.5) discloses an immunosensor based on a flexible electrode and use thereof, and belongs to the technical field of biosensors. The immunosensor includes a flexible electrode, the flexible electrode includes a flexible electrode substrate and a biomolecular probe fixed on a surface of the flexible electrode substrate, and the material of the flexible electrode substrate includes polylactic acid and graphene.

An electrode, as the core of an electrochemical sensor, can be made or modified with a nanomaterial or a composite material and the like so that the electrode has more functions to meet diverse experimental needs and detection needs; and these materials mainly include: graphene, graphene-gold nanoparticles, graphene-magnetic gold nanosphere composites, graphene-single stranded DNA, carbon nanotube-ionic liquid and the like, and electrochemical immunosensors based on these materials have the advantages of high sensitivity, high speed, high efficiency and the like. However, the stability of these materials as electrode modifying materials needs to be improved, or the antibody-antigen reaction specificity needs to be enhanced.

A Chinese patent document (application No.: 200910153183.X) discloses a method for preparing a nano-gold immunoelectrode, including the following steps: polishing a disk gold electrode with aluminum oxide powder, soaking with a mixture of concentrated sulfuric acid and hydrogen peroxide, performing ultrasonic cleaning, polishing with cyclic voltammetry in a 0.5 M sulfuric acid solution, by taking a chloroauric acid electrolyte as a base solution, depositing gold nanoparticles on the disk gold electrode with cyclic linear sweep voltammetry, connecting a specific antibody, and blocking.

Therefore, in order to achieve more functions of an electrode, it is necessary to provide an immunoelectrode to establish an immunoelectrode system and realize an electrochemical detection method with high detection sensitivity and stability.

SUMMARY

A first technical problem to be solved by the present invention is to provide an immunoelectrode to establish an immunoelectrode system and realize an electrochemical detection method with high detection sensitivity and stability.

To solve the technical problem, a technical solution adopted by the present invention is: the microfluidic detection chip further includes an immunoelectrode system, the immunoelectrode system includes a standard electrode and a working electrode, the standard electrode includes a gold-plated base layer, the working electrode includes a gold-plated base layer, a conductive polymer layer and an antibody layer, and the gold-plated base layer, the conductive polymer layer and the antibody layer are sequentially attached from bottom to top.

A further improvement of the present invention is that the immunoelectrode further includes a porous protective layer, and the porous protective layer is prepared on a surface of the antibody layer.

As a preferred technical solution of the present invention, the conductive polymer is polypyrrole or polythiophene or polyaniline.

In the above-mentioned technical solution, a conductive polymer layer is introduced into an immunoelectrode, a bio-recognition element antibody is fixed by the conductive polymer layer, and the antibody is immobilized on the electrode surface, to construct an immunoelectrode. In the present invention, the immunoelectrode adopts a three-electrode system, the gold-plated base layer is a composite electrode of a reference electrode and a counter electrode, and the antibody/conductive polymer/gold-plated base layer is a detection electrode; and a PS microsphere-marked antibody prepared based on an antigen-antibody specific reaction is subjected to an immunoreaction with the immunoelectrode and a sample antigen, to obtain a detection result of a sample indicator, and then a purpose of detection is achieved by detecting a change of a dielectric constant in the immunoelectrode system before and after the reaction. Meanwhile, through gold plating on a surface of a flexible base layer, the base layer is made to have electrical conductivity, and the gold nano layer or non-gold nano layer has good electrical conductivity and strong bioaffinity and can maintain protein activity to a certain extent, thereby improving the electrical conductivity and stability of the immunoelectrode. The upper layer is a bare gold-plated layer, the middle layer is a double-sided adhesive layer, the lower layer is an antibody/conductive polymer/gold-plated base layer, and the middle adhesive layer is hollowed out to form a flow channel and a reaction chamber, where the gold-plated base layer is a purchased finished product, and the gold is connected to the base layer by means of vacuum magnetron sputtering, electroplating, screen printing and the like.

A second technical problem to be solved by the present invention is to provide a method for preparing an immunoelectrode to establish an immunoelectrode system and realize an electrochemical detection method.

To solve the technical problem, a technical solution adopted by the present invention is: the method for preparing an immunoelectrode includes the following specific steps:

(1) preparation of a conductive polymer layer: a conductive polymer layer is prepared on a gold-plated base layer to obtain conductive polymer/gold-plated base layer;

(2) preparation of an immunoelectrode: an antibody layer is prepared on the conductive polymer layer to obtain antibody/conductive polymer/gold-plated base layer;

(3) porous modification on a surface: a surface of the antibody layer of the antibody/conductive polymer/gold-plated base layer is subjected to porous modification, polystyrene or polyaniline or tert-butyl polyacrylate or polycarbonate or polyvinyl alcohol is adopted as a film forming reagent material, chloroform or tetrahydrofuran or benzene or $CS_2$ is adopted as a solvent, and the film forming reagent material and the solvent are uniformly mixed and then dropwise added to a surface of the antibody/conductive polymer/gold-plated base layer so that a porous protective layer is obtained on the surface of the antibody layer of the antibody/conductive polymer/gold-plated base layer; and (4) formation of an immunoelectrode system: a bare gold-plated base layer is fixed to an outer side of the porous protective layer/antibody/conductive polymer/gold-plated base layer to obtain the immunoelectrode system.

In the above-mentioned technical solution, a conductive polymer layer is prepared on a gold-plated base layer so as to introduce the conductive polymer layer into an immunoelectrode, the conductive polymer material is mainly used to fix a bio-recognition element antibody and immobilize the antibody on a surface of the immunoelectrode, to form an immunoelectrode, and then, a purpose of detection is achieved by detecting a change of a dielectric constant in the immunoelectrode system before and after the reaction.

A further improvement of the present invention is that the method for preparing an immunoelectrode further includes a step (5): drawing of an immunoelectrode working curve: the immunoelectrode system is connected to an electrochemical working station, to obtain the immunoelectrode working curve, so as to achieve the purpose of detection. The prepared immunoelectrode is connected to the electrochemical working station, and the purpose of detection is achieved by detecting a change of a dielectric constant in the immunoelectrode system before and after the reaction.

As a preferred technical solution of the present invention, the step (1) includes the following specific steps:

S11. a gold-plated base layer is cleaned with ethanol and water, and dried in air for later use; and S12. the gold-plated base layer is put in a reaction and subjected to an overnight no-light reaction in a nitrogen atmosphere and under an ice-bath condition, the time of the overnight reaction being 10-16 h, and then rinsed with pure water and blown dry with nitrogen, so as to modify a surface of the gold-plated base layer with a conductive polymer, to obtain conductive polymer/gold-plated base layer.

As a preferred technical solution of the present invention, the step (2) includes the following specific steps:

S21. an antibody solution is dropwise added to a surface of the conductive polymer/gold-plated base layer obtained in the step (1), and it is allowed to stand at 37° C. and incubated for 1-2 h, and rinsed with a 0.1% Tween-20 solution to obtain antibody/conductive polymer/gold-plated base layer; and S22. a blocking buffer is dropwise added to a surface of the antibody/conductive polymer/gold-plated base layer immunoelectrode, and it is allowed to stand at 37° C. for 0.5-1.5 h to block inactive sites for later use.

As a preferred technical solution of the present invention, in the step (3), a mass fraction of the film forming reagent material in the solvent is 1-20%, the film forming reagent material and the solvent are uniformly mixed and then dropwise added to a surface of the antibody/conductive polymer/gold-plated base layer under the conditions of 25° C. and a relative humidity of 50-90%, and after the solvent is completely volatilized, a porous protective layer is formed on the surface of the antibody layer of the antibody/conductive polymer/gold-plated base layer.

As a preferred technical solution of the present invention, the step (5) includes the following specific steps:

S51. the immunoelectrode system is connected to an electrochemical working station;

S52. the area of a background CV curve of the immunoelectrode is measured with cyclic voltammetry by taking a buffer solution as a base solution; and S53. D-Dimer antigens of different concentrations are mixed with a PS microsphere-marked antibody solution, and the mixture is injected into the immunoelectrode system for binding with a coated antibody, to form gold-plated base layer-conductive polymer-antibody-porous protective layer-antigen-antibody microspheres, and after the reaction is completed, unbound protein samples are rinsed off with the buffer solution, the areas of CV curves of the immunoelectrode at different antigen concentrations are measured with cyclic voltammetry by taking the buffer solution as a base solution, and an immunoelectrode working curve is drawn so as to achieve a purpose of detection.

The present invention is described by taking the detection of an antigen indicator D-Dimer as an example, and is also applicable to the detection of other coagulation indicators and other disease indicators, including myocardial damage markers, gonadal hormones, thyroid function, infectious agents and the like.

As a preferred technical solution of the present invention, the PS microsphere-marked antibody solution used in the step S53 is prepared by the following steps:

S531. coating: microspheres and a D-Dimer antibody in a ratio of 1/3 are dissolved in a Mes buffer solution, and then are shaken for 20-40 min in an oscillator at 37° C. for coating;

S532. activation: 10-20 μL of an EDC solution is added to the solution after coating in the step S531 and shaken for 0.5-1.5 h in an oscillator at 37° C. for activation;

S533. blocking: 50-100 μL of a BSA solution is added to the solution after activation in the step S532 and shaken for 1-3 h in an oscillator at 37° C. for blocking; and S534. cleaning and storage: the solution after blocking in the step S533 is subjected to centrifugal cleaning, then placed in a latex preservation solution and put in a refrigerator at 0-4° C. for later use.

In the present invention, the PS microsphere-marked antibody is not fixed on a conductive polymer layer of a reaction cavity, but in a cavity (reaction cavity I) at a front end of a reaction cavity (reaction cavity II), and during a reaction, a sample first reacts with the PS microsphere-marked antibody, and then moves forward to the reaction cavity I and reacts with the fixed antibody on the conductive polymer layer.

As a preferred technical solution of the present invention, the base layer is a PET or PP or PE or ABS flexible base layer; the base layer is a PET flexible base layer; in the step S12, the composition of the reaction includes ferric chloride, a conductive polymer and hydrochloric acid, where the concentration of the ferric chloride is 0.01-0.5 mol/L, the concentration of the conductive polymer is 0.01-0.5 mol/L, and the concentration of the hydrochloric acid is 0.01-0.5 mol/L; in the step S21, 15 μL of a 0.024 mg/mL antibody is dropwise added to a surface of the conductive polymer/gold-plated base layer obtained in the step (1); in the step S22, a 2% BSA blocking buffer is dropwise added to a surface of the antibody/conductive polymer/gold-plated base layer; and in the step (3), the bare gold-plated base layer is fixed to an outer side of the antibody/conductive polymer/gold-plated base layer by using a double-sided adhesive, a reactive tank having a length of 0.1-0.8 cm and a width of 0.1-0.6 cm.

As a preferred technical solution of the present invention, in the step S12, the composition of the reaction includes ferric chloride, a conductive polymer, hydrochloric acid and sodium dodecyl sulfonate, and in the steps S52 and S53, the buffer solution is a PBS buffer solution, and the PBS buffer solution contains 0.1-0.15 mol/L NaCl as a supporting electrolyte. Adding the sodium dodecyl sulfonate to the reaction can change affinity, and adjusting the hydrophobicity of the conductive polymer can improve antibody fixing ability.

A third technical problem to be solved by the present invention is to provide a microfluidic detection chip applicable to an immunoelectrode, which can realize electrochemical detection and has the advantages of high detection sensitivity and stability, low interference between electrodes and high accuracy of the detection result.

To solve the technical problem, a technical solution adopted by the present invention is: the microfluidic detection chip adopting an immunoelectrode includes a lower-layer chip, a middle-layer chip and an upper-layer chip sequentially from bottom to top; the lower-layer chip, the middle-layer chip and the upper-layer chip cooperate with each other to define a closed micro-flow channel and a plurality of mutually independent chambers; the micro-flow channel and the chambers all penetrate through the middle-layer chip; a sample inlet is formed in the upper-layer chip and communicated with the chambers through the micro-flow channel; and the microfluidic detection chip further includes an immunoelectrode, the immunoelectrode includes a standard electrode and a working electrode, the standard electrode includes a gold-plated base layer, the working electrode includes a gold-plated base layer, a conductive polymer layer and an antibody layer, and the gold-plated base layer, the conductive polymer layer and the antibody layer are sequentially attached from bottom to top. In the above-mentioned technical solution, the detection of the microfluidic detection chip has the characteristics of high precision, high speed and low detection cost, and is suitable for detection on the links of precision medicine; by adopting a chip having the structure of a lower-layer chip, a middle-layer chip and an upper-layer chip, the design is reasonable, the structure is simple and compact, and the size of the microfluidic detection chip adopting an immunoelectrode can be reduced, so that the chip body is small and easy to carry, and the production cost is lowered; detection reagents are pre-embedded in the chambers, the chip structure is simple, the operation is convenient, the detection efficiency is improved, and the consumption of resources is greatly reduced; fast detection is realized, and the cost is lowered; and the electrode is an immunoelectrode, a conductive polymer layer, preferably polypyrrole, is introduced into the immunoelectrode, a bio-recognition element antibody is fixed by the conductive polymer layer, and the antibody is immobilized on the electrode surface, to construct an immunoelectrode. In the present invention, the immunoelectrode adopts a three-electrode system, the gold-plated base layer is a composite electrode of a reference electrode and a counter electrode, and the antibody/polypyrrole/gold-plated base layer is a detection electrode; a PS microsphere-marked antibody prepared based on an antigen-antibody specific reaction is subjected to an immunoreaction with the immunoelectrode and a sample antigen, to obtain a detection result of a sample indicator, and then a purpose of detection is achieved by detecting a change of a dielectric constant in the immunoelectrode system before and after the reaction. The polypyrrole has excellent electrical conductivity and can accelerate electron transfer on the electrode surface and improve the sensitivity of the immunoelectrode.

As a preferred technical solution of the present invention, each of the chambers includes a reaction cavity and a waste liquid cavity, the reaction cavity and the waste liquid cavity are both disposed on the middle-layer chip, the micro-flow channel includes a flow channel I, a stop valve site II is disposed on the flow channel I between the reaction cavity and the waste liquid cavity, and the immunoelectrode is divided into an upper-layer immunoelectrode disposed on the back of the upper-layer chip and a lower-layer immunoelectrode disposed on the front of the lower-layer electrode; a gap exists between the upper-layer immunoelectrode and the lower-layer immunoelectrode; the upper-layer immunoelectrode on the back of the upper-layer chip and the lower-layer immunoelectrode on the front of the lower-layer chip are both disposed corresponding to the position of the reaction cavity of the middle-layer chip, and the upper-layer immunoelectrode and the lower-layer immunoelectrode are communicated with each other through the reaction cavity; and the upper-layer immunoelectrode is a standard electrode, and the lower-layer immunoelectrode is a working electrode. A detection reagent is pre-embedded in the reaction cavity, and when to-be-detected blood flows into the reaction cavity, the upper-layer immunoelectrode and the lower-layer immunoelectrode both get into contact with the blood in the reaction cavity so as to be communicated through the electrical conductivity of the blood. Through the design of the upper-layer immunoelectrode and the lower-layer immunoelectrode, the electrodes of the microfluidic detection chip adopting an immunoelectrode are divided into two layers, and thus mutual interference between the electrodes can be reduced, and accuracy of the detection result is improved.

As a preferred technical solution of the present invention, the reaction cavity includes a reaction cavity I and a reaction cavity II, the micro-flow channel further includes a flow channel II, a stop valve site I is disposed on the flow channel II between the reaction cavity I and the reaction cavity II, the upper-layer immunoelectrode on the back of the upper-layer chip and the lower-layer immunoelectrode on the front of the lower-layer chip are both disposed corresponding to the position of the reaction cavity II of the middle-layer chip, and the upper-layer immunoelectrode and the lower-layer immunoelectrode are communicated with each other through the reaction cavity II. With provision of the stop valve site I, it can be ensured that, during a reaction in the reaction cavity I, a blood sample and the reacted reagent only exist in the reaction chamber 1 and do not flow into other chambers, and the reaction take places only in the reaction cavity I.

As a preferred technical solution of the present invention, each of the chambers further includes a cleaning solution cavity, the micro-flow channel further includes a sub-flow channel, the flow channel II extends outward from an outer side of the flow channel II between the reaction cavity II and the stop valve site I and is provided with the sub-flow channel, and the sub-flow channel is connected to the cleaning solution cavity. With provision of the stop valve site II, it can be ensured that, during a reaction in the reaction cavity II, a blood sample and the reacted reagent only exist in the reaction cavity II and do not flow into the waste liquid cavity, and it is also ensured that, during the reaction, waste liquid in the waste liquid cavity does not contaminate the reaction cavity II to avoid interfering with the reaction in the reaction cavity II. A cleaning solution in a form of a liquid sac is disposed in the cleaning solution cavity, and when in use, a power lever device of a matching detection instrument presses the liquid sac, and the joint between a front end of the liquid sac and the sub-flow channel cracks under the pressure so that liquid in the liquid sac flows out.

As a preferred technical solution of the present invention, the reaction cavity II is communicated with the waste liquid cavity through the flow channel I.

As a preferred technical solution of the present invention, an upper-layer communication hole is formed in the upper-layer chip, a lower-layer communication hole is formed in the lower-layer chip, the upper-layer immunoelectrode is in contact connection to the matching detection instrument through the lower-layer communication hole; and the lower-layer immunoelectrode is in contact connection to the matching detection instrument through the upper-layer communication hole. Through such a setting, the immunoelectrode can be connected to the matching instrument through the upper-layer communication hole and the lower-layer communication hole without a need to set an additional end for connecting the matching instrument.

As a preferred technical solution of the present invention, a liquid receiving port is formed in the middle-layer chip and disposed corresponding to the position of the sample inlet, the micro-flow channel further includes a flow channel III, and the reaction cavity I is communicated with the liquid receiving port through the flow channel III.

As a preferred technical solution of the present invention, each of the chambers further includes a buffer solution cavity, the sub-flow channel extends outward from an outer side of the sub-flow channel and is provided with a sub-flow channel I, and the sub-flow channel I is connected to the buffer solution cavity. A buffer solution in a form of a liquid sac is disposed in the buffer solution cavity, and when in use, a power lever device of a matching detection instrument presses the liquid sac, and the joint between a front end of the liquid sac and the sub-flow channel cracks under the pressure so that liquid in the liquid sac flows out.

As a preferred technical solution of the present invention, at least one vent hole is formed in the upper-layer chip, and the vent hole is disposed at one end of the upper-layer chip and in a position corresponding to the waste liquid cavity. By disposing at least one vent hole penetrating through the upper-layer chip, flow resistance against a to-be-detected fluid is reduced, and the fluid flows faster to quickly fill the chambers; and the vent hole is favorable for the flow of a sample to facilitate sample introduction. Without the vent hole, the sample cannot flow into the reaction cavity for a reaction. A detection reagent is pre-embedded in the reaction cavity.

As a preferred technical solution of the present invention, a sample introduction cover is disposed on the sample inlet and covers the sample inlet after sample introduction, to allow a sample to flow.

As a preferred technical solution of the present invention, the gold-plated base layer includes a base layer and a gold layer; and the working electrode further includes a porous protective layer, and the porous protective layer is disposed on a surface of the antibody layer. The gold-plated base layer is a purchased finished product, and the gold is connected to the base layer by means of vacuum magnetron sputtering, electroplating, screen printing and the like; the base layer is a flexible base layer and is made from a material of PET, PP, PE, ABS and the like, where PET is hard and has strong bending resistance, and its surface is flat for coating; through gold plating on a surface of a flexible base layer, the base layer is made to have electrical conductivity, and the gold nano layer or non-gold nano layer has good electrical conductivity and strong bioaffinity and can maintain protein activity to a certain extent, thereby improving the electrical conductivity and stability of the immunoelectrode; and the porous protective layer is obtained by performing porous modification treatment on a surface of the antibody layer.

As a preferred technical solution of the present invention, the lower-layer chip, the middle-layer chip and the upper-layer chip are bonded together through double-sided gluing by means of the middle-layer chip.

As a preferred technical solution of the present invention, the middle-layer chip is a double-sided adhesive, the material of the upper-layer chip and/or the lower-layer chip is any one of PMMA, PP, PE and PET, and a hydrophilic film is disposed on the surfaces of the upper-layer chip and the lower-layer chip respectively, so that a sample quickly passes through the sample inlet and flows into the micro-flow channel and then into the chambers. The middle-layer chip is preferably a pressure sensitive adhesive tape. With the technical solution, the materials are easily available, and the production technology of the pressure sensitive adhesive tape can precisely control the thickness thereof. Therefore, by adopting the technical solution, the depth and size of the micro-flow channel can be accurately controlled while it is convenient to control the depth of the chambers, so that the chambers of the microfluidic detection chip have a small difference in thickness and are highly consistent, thereby improving the accuracy of detection; and a hydrophilic film is disposed on the surfaces of the upper-layer chip and the lower-layer chip respectively, so that a sample can quickly pass through the sample inlet and flow into the micro-flow channel and the chambers, thereby increasing the flow speed and improving the detection efficiency.

As a preferred technical solution of the present invention, the thickness of the middle-layer chip is 0.1-1.0 mm; and the surface of the lower-layer chip is flat, and the closed micro-flow channel defined through mutual cooperation of the lower-layer chip, the middle-layer chip and the upper-layer chip has a depth of 0.1-1.0 mm, and the chambers defined through mutual cooperation have a width of 1.0-2.0 mm.

Compared with the prior art, the present invention has the following beneficial effects: the technical solutions of the present invention propose the construction and use of an electrochemical immunoelectrode based on a polypyrrole material; the polypyrrole material is used to fix a bio-recognition element antibody and immobilize same on an electrode, and due to the excellent electrical conductivity of polypyrrole, electron transfer on the electrode surface can be accelerated, and the sensitivity of the immunoelectrode is improved; thus, polypyrrole (conductive polymer) is introduced into the preparation of an immunoelectrode, to prepare an electrochemical immunoelectrode system containing a polypyrrole material, and the immunoelectrode system is easy to operate, simplifies the detection steps and is favorable for mass detection; a purpose of detection is achieved by use of a change of a dielectric constant in the immunoelectrode system; the microfluidic detection chip adopting an immunoelectrode improves the accuracy of the detection result; meanwhile, through the design of the reaction chambers, the waste liquid cavity, the cleaning solution cavity and the buffer solution cavity in a specific structural form, a detection reaction is completed in one microfluidic detection chip to obtain a reaction result; the chip is simple in structure and easy to operate, improves the efficiency and precision of detection and greatly reduces the consumption of resources; and fast detection is realized, and the cost is lowered.

in the figures, 1—Lower-layer chip; 101—Lower-layer communication hole; 2—Middle-layer chip; 201—Middle-layer communication hole; 202—Liquid receiving port; 3—Upper-layer chip; 301—Upper-layer communication hole; 4—Upper-layer immunoelectrode; 5—Lower-layer immunoelectrode; 6—Micro-flow channel; 601—Flow channel I; 602—Flow channel II; 603—Flow channel III; 604—Sub-flow channel; 605—Sub-flow channel I; 7—Vent hole; 8—Sample inlet; 901—Reaction cavity I; 902—Reaction cavity II; 903—Waste liquid cavity; 904—Buffer solution cavity; 905—Cleaning solution cavity; 10—Base layer; 11—Gold layer; 12—Conductive polymer layer; 13—Antibody layer; and 14—Porous protective layer.

DESCRIPTION OF THE EMBODIMENTS

Figure 1:
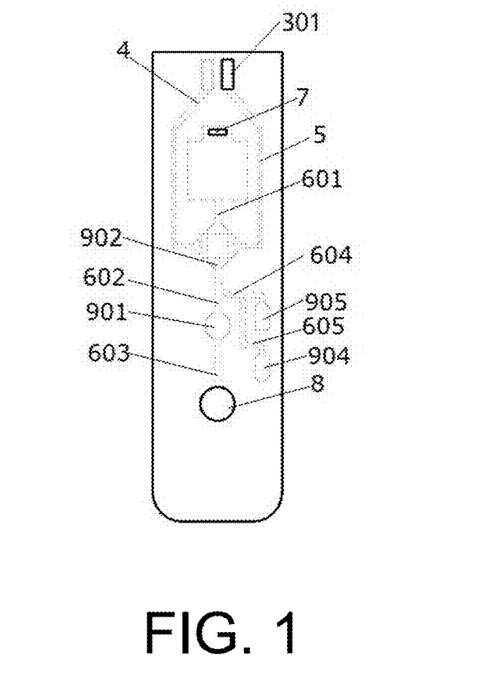
FIG. 1 is a schematic diagram of a perspective structure of the entire front of a microfluidic detection chip adopting an immunoelectrode according to the present invention.
Figure 2:
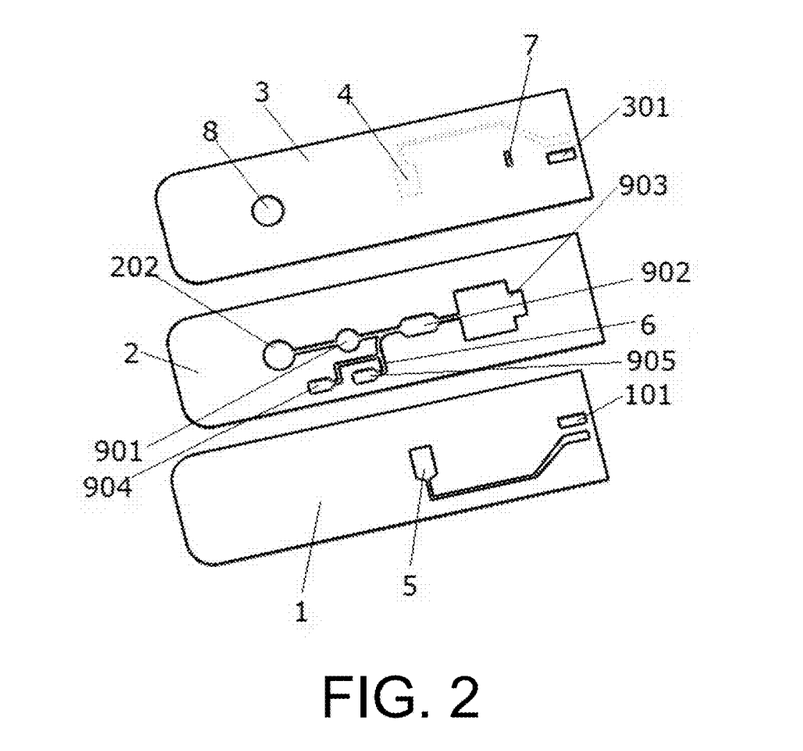
FIG. 2 is a schematic diagram of a three-layer exploded structure of a microfluidic detection chip adopting an immunoelectrode according to the present invention.
Figure 3:
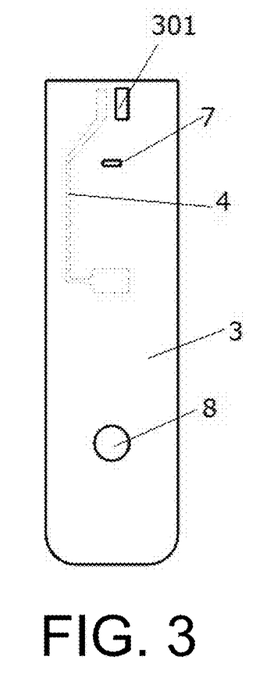
FIG. 3 is a schematic diagram of a front structure of an upper-layer chip of a microfluidic detection chip adopting an immunoelectrode according to the present invention.
Figure 4:
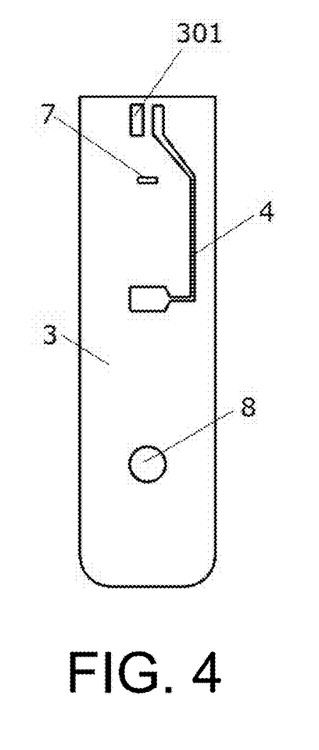
FIG. 4 is a schematic diagram of a back structure of an upper-layer chip of a microfluidic detection chip adopting an immunoelectrode according to the present invention.
Figure 5:
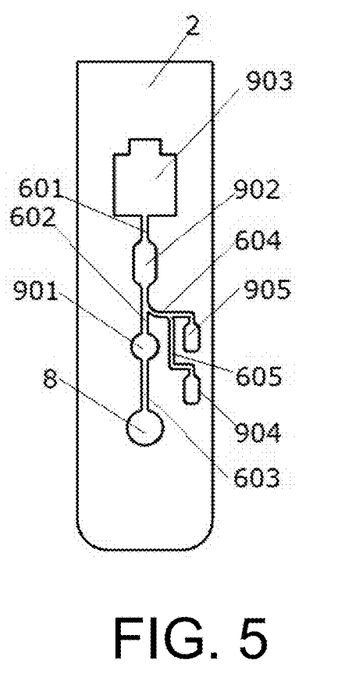
FIG. 5 is a schematic diagram of a front structure of a middle-layer chip of a microfluidic detection chip adopting an immunoelectrode according to the present invention.
Figure 6:
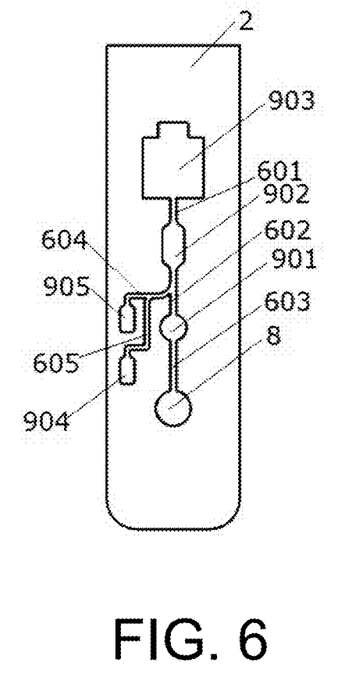
FIG. 6 is a schematic diagram of a back structure of a middle-layer chip of a microfluidic detection chip adopting an immunoelectrode according to the present invention.
Figure 7:
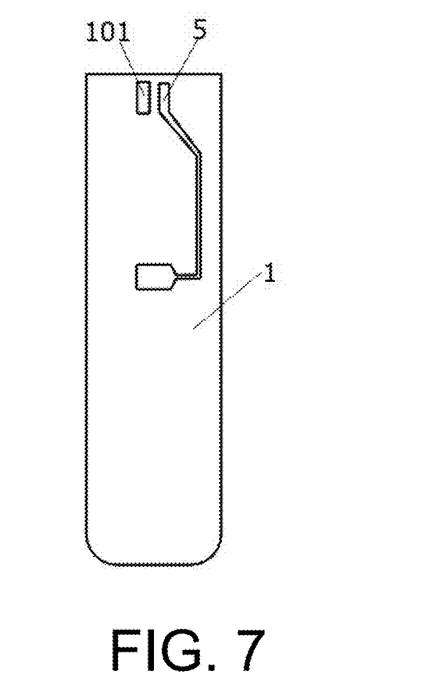
FIG. 7 is a schematic diagram of a front structure of a lower-layer chip of a microfluidic detection chip adopting an immunoelectrode according to the present invention.
Figure 8:
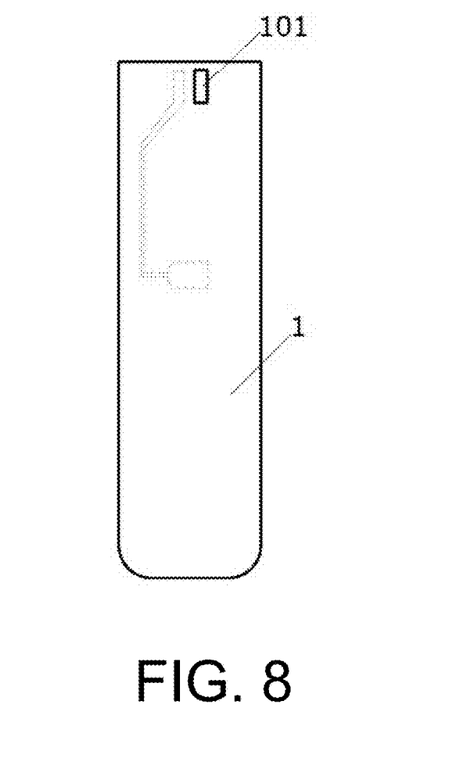
FIG. 8 is a schematic diagram of a back structure of a lower-layer chip of a microfluidic detection chip adopting an immunoelectrode according to the present invention.
Figure 9:
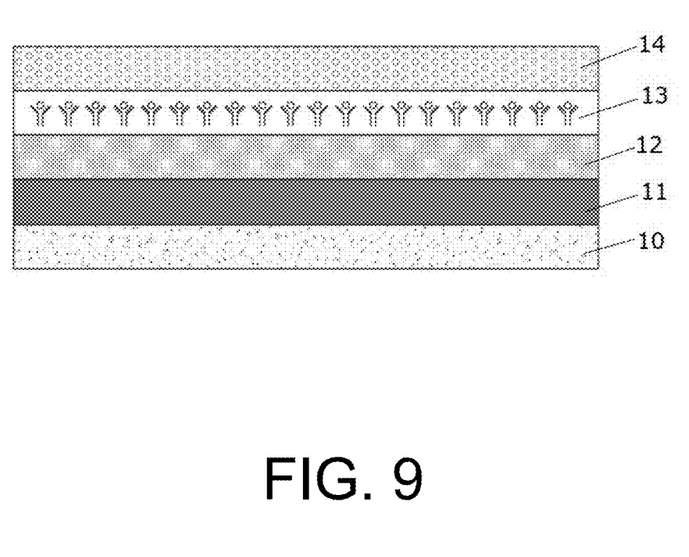
FIG. 9 is a structural diagram of an immunoelectrode according to the present invention.

Example 1: As shown in FIG. 9, the immunoelectrode includes a base layer 10, a gold layer 11, a conductive polymer layer 12, an antibody layer 13 and a porous protective layer 14, the base layer 10, the gold layer 11, the conductive polymer layer 12, the antibody layer 13 and the porous protective layer 14 are sequentially attached from bottom to top, and the base layer 10 is a PET flexible base layer; and the conductive polymer layer 12 is a polypyrrole layer.

Example 2: A method for preparing a polypyrrole-based immunoelectrode of Example 1 includes the following steps:
  (1) synthesis of a polypyrrole layer (conductive polymer layer): a polypyrrole layer was prepared on a gold-plated base layer after gold plating, to obtain polypyrrole/gold-plated base layer;
  S11. the gold-plated PET base layer was subjected to ultrasonic cleaning sequentially using ethanol and ultrapure water, and dried in air for later use; and
  S12. the gold-plated PET base layer dried in air for later use was fixed at the bottom of a 1,000 mL flask, and a reaction was added into the flask, the reaction including pure water, hydrochloric acid, ferric trichloride and pyrrole; 400 mL of pure water and 6.4 mL of 1 mol/L hydrochloric acid were added into the flask and stirred uniformly, then 0.88 g of ferric trichloride was slowly added and stirred uniformly, the flask was put under an ice-bath condition, 400 µL of pyrrole was slowly added in a nitrogen atmosphere, and then an overnight no-light reaction was performed in an ice-bath nitrogen atmosphere, the time of the overnight reaction being 10-16 h; then, the resulting product was repeatedly washed with pure water, and dried in a nitrogen atmosphere, to form a black polypyrrole layer on a surface of the gold-plated PET base layer and obtain polypyrrole/gold-plated base layer;
  (2) preparation of an immunoelectrode: an antibody layer 13 was prepared on the polypyrrole layer to obtain antibody/polypyrrole/gold-plated base layer;
  S21. 15 µL of a 0.024 mg/mL unmarked D-Dimer antibody solution was dropwise added to a surface of the polypyrrole/gold-plated base layer obtained in the step (1), and it was allowed to stand at 37° C. and incubated for 1.5 h, and rinsed with a 0.1% Tween-20 solution to obtain antibody/polypyrrole/gold-plated base layer; and S22. a BSA blocking buffer was dropwise added to a surface of the antibody/polypyrrole/gold-plated base layer immunoelectrode, and it was allowed to stand at 37° C. for 1 h to block inactive sites, to obtain a D-Dimer antibody/polypyrrole/gold-plated PET immunoelectrode for later use;

(3) porous modification on a surface: a surface of the antibody layer 13 of the antibody/conductive polymer/gold-plated base layer was subjected to porous modification, polystyrene or polyaniline or tert-butyl polyacrylate or polycarbonate or polyvinyl alcohol was adopted as a film forming reagent material, chloroform or tetrahydrofuran or benzene or $CS_2$ was adopted as a solvent, and the film forming reagent material and the solvent were uniformly mixed and then dropwise added to a surface of the antibody/conductive polymer/gold-plated base layer so that a porous protective layer 14 was obtained on the surface of the antibody layer of the antibody/conductive polymer/gold-plated base layer; and in the step (3), a mass fraction of the film forming reagent material in the solvent was 15%, the film forming reagent material and the solvent were uniformly mixed and then dropwise added to a surface of the antibody/conductive polymer/gold-plated base layer under the conditions of 25° C. and a relative humidity of 65-75%, and after the solvent was completely volatilized, a porous protective layer 14 was formed on the surface of the antibody layer 13 of the antibody/conductive polymer/gold-plated base layer;

(4) formation of an immunoelectrode system: a gold-plated base layer was fixed to an outer side of the porous protective layer 14/D-Dimer antibody/polypyrrole/gold-plated base layer to obtain the immunoelectrode system, a reaction tank having an area of 0.56 cm*0.3 cm; and (5) drawing of an immunoelectrode working curve: the immunoelectrode system was connected to an electrochemical working station, to obtain the immunoelectrode working curve, so as to achieve a purpose of detection;

S51. the immunoelectrode system was connected to an electrochemical working station;

S52. the area of a background CV curve of the immunoelectrode was measured with cyclic voltammetry by taking a PBS buffer solution of pH 7.6 as a base solution, the PBS buffer solution containing 0.15 mol/L NaCl as a supporting electrolyte; and S53. D-Dimer antigens of different concentrations were mixed with a PS microsphere-marked antibody solution, and injected into the immunoelectrode system for binding with a coated antibody, to form gold-plated base layer-polypyrrole-antibody-porous protective layer-antigen-antibody microspheres, and after the reaction was completed, unbound protein samples were rinsed off with the buffer solution, the areas of CV curves of the immunoelectrode at different antigen concentrations were measured with cyclic voltammetry by taking the buffer solution as a base solution, and the immunoelectrode working curve was drawn so as to achieve a purpose of detection.

Example 3: A difference from Example 2 lies in that the conductive polymer layer in the immunoelectrode adopts sodium dodecyl sulfonate-doped polypyrrole; and the method for preparing the polypyrrole-based immunoelectrode includes the following steps:

(1) preparation of a conductive polymer layer: a polypyrrole layer was prepared on a gold-plated base layer, to obtain polypyrrole/gold-plated base layer;

S11. the gold-plated PET base layer was subjected to ultrasonic cleaning sequentially using ethanol and ultrapure water, and dried in air for later use; and S12. the gold-plated PET base layer dried in air for later use was fixed at the bottom of a 1,000 mL flask, and a reaction was added into the flask, the reaction including pure water, hydrochloric acid, ferric trichloride, pyrrole and sodium dodecyl sulfonate (SDS); 400 mL of pure water and 6.4 mL of 1 mol/L hydrochloric acid were added into the flask and stirred uniformly, then 0.88 g of ferric trichloride and 0.17 g of sodium dodecyl sulfonate (SDS) were slowly added and stirred uniformly, the flask was put under an ice-bath condition, 400 µL of pyrrole was slowly added in a nitrogen atmosphere, and an overnight no-light reaction was performed in an ice-bath nitrogen atmosphere, the time of the overnight reaction being 10-16 h; then, the resulting product was repeatedly washed with pure water, and dried in a nitrogen atmosphere, to form an SDS-doped polypyrrole layer on the gold-plated PET surface and obtain doped polypyrrole/gold-plated base layer;

(2) preparation of an immunoelectrode: an antibody layer 13 was prepared on the SDS-doped polypyrrole layer to obtain antibody/doped polypyrrole/gold-plated base layer;

S21. 15 µL of a 0.024 mg/mL unmarked D-Dimer antibody solution was dropwise added to a surface of the polypyrrole/gold-plated base layer obtained in the step (1), and it was allowed to stand at 37° C. and incubated for 1.5 h, and rinsed with a 0.1% Tween-20 solution to obtain antibody/SDS-doped polypyrrole/gold-plated base layer; and S22. a BSA blocking buffer was dropwise added to a surface of the antibody/SDS-doped polypyrrole/gold-plated base layer immunoelectrode, and it was allowed to stand at 37° C. for 1 h to block inactive sites, to obtain a D-Dimer antibody/SDS-doped polypyrrole/gold-plated PET immunoelectrode for later use;

(3) porous modification on a surface: a surface of the antibody layer 13 of the antibody/conductive polymer/gold-plated base layer was subjected to porous modification, polystyrene or polyaniline or tert-butyl polyacrylate or polycarbonate or polyvinyl alcohol was adopted as a film forming reagent material, chloroform or tetrahydrofuran or benzene or $CS_2$ was adopted as a solvent, and the film forming reagent material and the solvent were uniformly mixed and then dropwise added to a surface of the antibody/conductive polymer/gold-plated base layer so that a porous protective layer 14 was obtained on the surface of the antibody layer of the antibody/conductive polymer/gold-plated base layer; and in the step (3), a mass fraction of the film forming reagent material in the solvent was 15%, the film forming reagent material and the solvent were uniformly mixed and then dropwise added to a surface of the antibody/conductive polymer/gold-plated base layer under the conditions of 25° C. and a relative humidity of 65-75%, and after the solvent was completely volatilized, a porous protective layer 14 was formed on the surface of the antibody layer 13 of the antibody/conductive polymer/gold-plated base layer;

(4) formation of an immunoelectrode system: a gold-plated base layer was fixed to an outer side of the porous protective layer/D-Dimer antibody/polypyrrole/ gold-plated base layer to obtain the immunoelectrode system, a reaction tank having an area of 0.56 cm*0.3 cm; and (5) drawing of an immunoelectrode working curve: the immunoelectrode system was connected to an electrochemical working station, to obtain the immunoelectrode working curve so as to achieve a purpose of detection;

S51. the immunoelectrode system was connected to an electrochemical working station;

S52. the area of a background CV curve of the immunoelectrode was measured with cyclic voltammetry by taking a PBS buffer solution of pH 7.6 as a base solution, the PBS buffer solution containing 0.15 mol/L NaCl as a supporting electrolyte; and S53. D-Dimer antigens of different concentrations were mixed with a PS microsphere-marked antibody solution, and injected into the immunoelectrode system for binding with a coated antibody, to form gold-plated base layer-polypyrrole-antibody-porous protective layer-antigen-antibody microspheres, and after the reaction was completed, unbound protein samples were rinsed off with the buffer solution, the areas of CV curves of the immunoelectrode at different antigen concentrations were measured with cyclic voltammetry by taking the buffer solution as a base solution, and the immunoelectrode working curve was drawn so as to achieve a purpose of detection, where the PS microsphere-marked antibody solution used in the step S53 was prepared by the following steps:

S531. coating: 5% P0112 microspheres (Model: P0112; Manufacturer: ThermoFisher) and a 5.1 mg/mL D-Dimer antibody (Model: A8D04M; Manufacturer: Suzhou Lanxuan Biotechnology Co., Ltd.) in a ratio of 1/3 were dissolved in 0.5 mL (pH 6.0) of a Mes buffer solution, and then shaken for 30 min in an oscillator at 37° C. for coating;

S532. activation: 16 μL of a 10 mg/mL EDC solution was added to the solution after coating in the step S531 and shaken for 1 h in an oscillator at 37° C. for activation;

S533. blocking: 87 μL of a 100 mg/mL BSA solution was added to the solution after activation in the step S532 and shaken for 2 h in an oscillator at 37° C. for blocking; and S534. cleaning and storage: the solution after blocking in the step S533 was subjected to centrifugal cleaning, then placed in a latex preservation solution and put in a refrigerator at 4° C. for later use.

Example 4: A method for detecting a D-Dimer antigen with the immunoelectrode system of Example 3 includes the following specific steps:

1) a three-electrode system (a working electrode, a reference electrode and a counter electrode, where the reference electrode and the counter electrode were a composite electrode thereof) was adopted for immunodetection, D-Dimer antibody/SDS-doped polypyrrole/gold-plated PET being a working electrode, and bare gold-plated PET being a composite electrode of the reference electrode and the counter electrode; and a PBS buffer solution containing 150 mM NaCl was added to the detection system, the immunoelectrode was subjected to continuous CV sweep, and a CV curve thereof was recorded, and a corresponding CV curve area was calculated and recorded, where a sweep range was 0-1 V, and a potential sweep speed was 50 mV/s;

2) the prepared immunoelectrode was correctly connected to an electrochemical working station, a PBS buffer solution was added to the immunoelectrode system, CV curve sweep was performed, a CV curve obtained by stable sweep was recorded, and the CV area thereof was calculated;

3) after the recording, a D-Dimer antigen and a PS microsphere-marked antibody were mixed and added to the immunoelectrode and allowed to react for 10 min at room temperature, then unbound protein samples were rinsed off with the PBS buffer solution, a CV curve sweep was performed again in an environment with the PBS buffer solution, and a corresponding CV curve area was recorded and calculated; and 4) detection of an electrochemical signal of the immunoelectrode was based on a double-antibody sandwich reaction mode, and an antigen in a sample solution was bound to the PS microsphere-marked antibody and then experienced an immunoreaction with an antibody immobilized on the electrode surface.

Example 5: As shown in FIGS. 1-8, the microfluidic detection chip adopting the immunoelectrode of Example 1 or 2 or 3 includes a lower-layer chip 1, a middle-layer chip 2 and an upper-layer chip 3 sequentially from bottom to top; the lower-layer chip 1, the middle-layer chip 2 and the upper-layer chip 3 cooperate with each other to define a closed micro-flow channel and a plurality of mutually independent chambers; the micro-flow channel 6 and the chambers all penetrate through the middle-layer chip 2; a sample inlet 8 is formed in the upper-layer chip 3 and communicated with the chambers through the micro-flow channel 6; the microfluidic detection chip further includes an immunoelectrode, the immunoelectrode includes a standard electrode and a working electrode, the standard electrode includes a gold-plated base layer, the working electrode includes a gold-plated base layer, a conductive polymer layer 12 and an antibody layer 13, the gold-plated base layer includes a base layer 10 and a gold layer 11, the base layer 10, the gold layer 11, the conductive polymer layer 12 and the antibody layer 13 are sequentially attached from bottom to top, and the base layer 10 is a PET flexible base layer; each of the chambers includes a reaction cavity and a waste liquid cavity 903, the reaction cavity and the waste liquid cavity 903 are both disposed on the middle-layer chip 2, the micro-flow channel 6 includes a flow channel I 601, a stop valve site II is disposed on the flow channel I 601 between the reaction cavity and the waste liquid cavity 903, and the immunoelectrode is divided into an upper-layer immunoelectrode 4 disposed on the back of the upper-layer chip 3 and a lower-layer immunoelectrode 5 disposed on the back of the lower-layer chip 1; a gap exists between the upper-layer immunoelectrode 4 and the lower-layer immunoelectrode 5; the upper-layer immunoelectrode 4 on the back of the upper-layer chip 3 and the lower-layer immunoelectrode 5 on the front of the lower-layer chip 1 are both disposed corresponding to the position of the reaction cavity of the middle-layer chip 2, and the upper-layer immunoelectrode 4 and the lower-layer immunoelectrode 5 are communicated with each other through the reaction cavity; the upper-layer immunoelectrode 4 is a standard electrode, and the lower-layer immunoelectrode 5 is a working electrode; a detection reagent is pre-embedded in the reaction cavity, and when to-be-detected blood flows into the reaction cavity, the upper-layer immunoelectrode 4 and the lower-layer immunoelectrode 5 both get into contact with the blood in the reaction cavity so as to be communicated through the electrical conductivity of the blood; the reaction cavity includes a reaction cavity I 901 and a reaction cavity II 902, the micro-flow channel further includes a flow channel II 602, a stop valve site I is disposed on the flow channel II 602 between the reaction cavity I 901 and the reaction cavity II 902, the upper-layer immunoelectrode 4 on the back of the upper-layer chip 3 and the lower-layer immunoelectrode 5 on the front of the lower-layer chip 1 are both disposed corresponding to the position of the reaction cavity II 902 of the middle-layer chip 2, and the upper-layer immunoelectrode 4 and the lower-layer immunoelectrode 5 are communicated with each other through the reaction cavity II 902; each of the chambers further includes a cleaning solution cavity 905, the micro-flow channel 6 further includes a sub-flow channel 604, the flow channel II 602 extends outward from an outer side of the flow channel II 602 between the reaction cavity II 902 and the stop valve site I and is provided with the sub-flow channel 604, and the sub-flow channel 604 is connected to the cleaning solution cavity 905; the reaction cavity II 902 is communicated with the waste liquid cavity 903 through the flow channel I 601; an upper-layer communication hole 301 is formed in the upper-layer chip 3, a lower-layer communication hole 101 is formed in the lower-layer chip 1, and the upper-layer immunoelectrode 4 is in contact connection to a matching detection instrument through the lower-layer communication hole 101; the lower-layer immunoelectrode 5 is in contact connection to the matching detection instrument through the upper-layer communication hole 301; a liquid receiving port 202 is formed in the middle-layer chip 2 and disposed corresponding to the position of the sample inlet 8, the micro-flow channel 6 further includes a flow channel III 603, and the reaction cavity I 901 is communicated with the liquid receiving port 202 through the flow channel III 603; each of the chambers further includes a buffer solution cavity 904, the sub-flow channel 604 extends outward from an outer side of the sub-flow channel 604 and is provided with a sub-flow channel I 605, and the sub-flow channel I 605 is connected to the buffer solution cavity 904; at least one vent hole 7 is formed in the upper-layer chip 3, and the vent hole 7 is disposed at one end of the upper-layer chip 3 and in a position corresponding to the waste liquid cavity 903; the vent hole 7 is favorable for the flow of a sample to facilitate sample introduction; a sample introduction cover is disposed on the sample inlet 8 and covers the sample inlet 8 after sample introduction, to allow a sample to flow; and the immunoelectrode further includes a porous protective layer, and the porous protective layer is prepared on a surface of the antibody layer.

Example 6: A microfluidic detection chip adopting the immunoelectrode of Example 1 or 2 or 3 includes a lower-layer chip 1, a middle-layer chip 2 and an upper-layer chip 3 sequentially from bottom to top; the lower-layer chip 1, the middle-layer chip 2 and the upper-layer chip 3 cooperate with each other to define a closed micro-flow channel and a plurality of mutually independent chambers; the micro-flow channel 6 and the chambers all penetrate through the middle-layer chip 2; a sample inlet 8 is formed in the upper-layer chip 3 and communicated with the chambers through the micro-flow channel 6; the microfluidic detection chip further includes an immunoelectrode system, the immunoelectrode system includes a standard electrode and a working electrode, the standard electrode includes a gold-plated base layer, the working electrode includes a gold-plated base layer, a conductive polymer layer 12, an antibody layer 13 and a porous protective layer 14, the gold-plated base layer includes a base layer 10 and a gold layer 11, the base layer 10, the gold layer 11, the conductive polymer layer 12, the antibody layer 13 and the porous protective layer 14 are sequentially attached from bottom to top, and the base layer 10 is a PET flexible base layer; each of the chambers includes a reaction cavity and a waste liquid cavity 903, the reaction cavity and the waste liquid cavity 903 are both disposed on the middle-layer chip 2, the micro-flow channel 6 includes a flow channel I 601, a stop valve site II is disposed on the flow channel I 601 between the reaction cavity and the waste liquid cavity 903, and the immunoelectrode is are divided into an upper-layer immunoelectrode 4 disposed on the back of the upper-layer chip 3 and a lower-layer immunoelectrode 5 disposed on the back of the lower-layer chip 1; a gap exists between the upper-layer immunoelectrode 4 and the lower-layer immunoelectrode 5; the upper-layer immunoelectrode 4 on the back of the upper-layer chip 3 and the lower-layer immunoelectrode 5 on the front of the lower-layer chip 1 are both disposed corresponding to the position of the reaction cavity of the middle-layer chip 2, and the upper-layer immunoelectrode 4 and the lower-layer immunoelectrode 5 are communicated with each other through the reaction cavity; the upper-layer immunoelectrode 4 is a standard electrode, and the lower-layer immunoelectrode 5 is a working electrode; a detection reagent is pre-embedded in the reaction cavity, and when to-be-detected blood flows into the reaction cavity, the upper-layer immunoelectrode 4 and the lower-layer immunoelectrode 5 both get into contact with the blood in the reaction cavity so as to be communicated through the electrical conductivity of the blood; the reaction cavity includes a reaction cavity I 901 and a reaction cavity II 902, the micro-flow channel further includes a flow channel II 602, a stop valve site I is disposed on the flow channel II 602 between the reaction cavity I 901 and the reaction cavity II 902, the upper-layer immunoelectrode 4 on the back of the upper-layer chip 3 and the lower-layer immunoelectrode 5 on the front of the lower-layer chip 1 are both disposed corresponding to the position of the reaction cavity II 902 of the middle-layer chip 2, and the upper-layer immunoelectrode 4 and the lower-layer immunoelectrode 5 are communicated with each other through the reaction cavity II 902; each of the chambers further includes a cleaning solution cavity 905, the micro-flow channel 6 further includes a sub-flow channel 604, the flow channel II 602 extends outward from an outer side of the flow channel II 602 between the reaction cavity II 902 and the stop valve site I and is provided with the sub-flow channel 604, and the sub-flow channel 604 is connected to the cleaning solution cavity 905; the reaction cavity II 902 is communicated with the waste liquid cavity 903 through the flow channel I 601; an upper-layer communication hole 301 is formed in the upper-layer chip 3, a lower-layer communication hole 101 is formed in the lower-layer chip 1, and the upper-layer immunoelectrode 4 is in contact connection to a matching detection instrument through the lower-layer communication hole 101; the lower-layer immunoelectrode 5 is in contact connection to the matching detection instrument through the upper-layer communication hole 301; a liquid receiving port 202 is formed in the middle-layer chip 2 and disposed corresponding to the position of the sample inlet 8, the micro-flow channel 6 further includes a flow channel III 603, and the reaction cavity I 901 is communicated with the liquid receiving port 202 through the flow channel III 603; each of the chambers further includes a buffer solution cavity 904, the sub-flow channel 604 extends outward from an outer side of the sub-flow channel 604 and is provided with a sub-flow channel I 605, and the sub-flow channel I 605 is connected to the buffer solution cavity 904; at least one vent hole 7 is formed in the upper-layer chip 3, and the vent hole 7 is disposed at one end of the upper-layer chip 3 and in a position corresponding to the waste liquid cavity 903; the vent hole 7 is favorable for the flow of a sample to facilitate sample introduction; a sample introduction cover is disposed on the sample inlet 8 and covers the sample inlet 8 after sample introduction, to allow a sample to flow; the immunoelectrode further includes a porous protective layer, and the porous protective layer is prepared on a surface of the antibody layer; the lower-layer chip 1, the middle layer chip 2 and the upper-layer chip 3 are bonded together through double-sided gluing by means of the middle-layer chip 2; and the middle-layer chip 2 is a double-sided adhesive, the material of the upper-layer chip 3 and/or the lower-layer chip 1 is any one of PMMA, PP, PE and PET, and a hydrophilic film is disposed the surfaces of the upper-layer chip 3 and the lower-layer chip 1 respectively, so that a sample quickly passes through the sample inlet 8 and flows into the micro-flow channel 6 and then into the chambers. The middle-layer chip 2 is preferably a pressure sensitive adhesive tape. With the technical solution, the materials are easily available, and the production technology of the pressure sensitive adhesive tape can precisely control the thickness thereof. Therefore, by adopting the technical solution, the depth and size of the micro-flow channel can be accurately controlled while it is convenient to control the depth of the chambers, so that the chambers of the microfluid detection chip have a small difference in thickness and are highly consistent, thereby improving the accuracy of detection; a hydrophilic film is disposed on the surfaces of the upper-layer chip 3 and the lower-layer chip 1 respectively; the thickness of the middle-layer chip 2 is 0.1-1.0 mm; and the surface of the lower-layer chip 1 is flat, the closed micro-flow channel 6 defined through mutual cooperation of the lower-layer chip 1, the middle-layer chip 2 and the upper-layer chip 3 has a depth of 0.1-1.0 mm, and the chambers defined through mutual cooperation have a width of 1.0-2.0 mm.

When in use: the stop valve site I is turned off at first, a power lever device of a matching detection instrument acts to crack a buffer solution sac in the buffer solution cavity 904, the power lever drives the liquid so that a buffer solution in the solution sac enters the reaction cavity II 902, then the stop valve site II is turned off, data on the detection instrument is read within 30 seconds, and the stop valve site 2 is turned on so that the liquid in the reaction cavity II 902 enters the waste liquid cavity 903; a blood sample is injected into the sample inlet 8 and the sample inlet 8 is covered with the sample introduction cover, the sample flows from the liquid receiving port 202 toward the reaction cavity I 901 through the flow channel III 603 and reacts with a fixed antibody therein for 1-5 min, after the reaction is completed, the stop valve site I is turned on, the sample enters the reaction cavity II 902, the stop valve site I is turned off while it is ensured that the stop valve site II is kept in a closed state, a reaction takes place for 1-5 min, and the stop valve site II is turned on; the power lever device of the matching detection instrument acts to crack a cleaning solution sac in the cleaning solution cavity 905, a cleaning solution therein enters the reaction cavity II 902 and cleans the immunoelectrode, the cleaning waste liquid enters the waste liquid cavity, the instrument receives an electrical signal in the reaction cavity, and an instrument software calculates the content of a sample indicator.

The basic principles, main features and advantages of the present invention are shown and described above. Those skilled in the art should understand that the present invention is not limited to the above-mentioned examples, and the above-mentioned examples and the descriptions in the specification are only for description of the principles of the present invention. On the premise of not departing from the spirit and scope of the present invention, various changes and improvements to the present invention are possible, such as some other slight adjustments to the layout structures of the chambers, to the configuration of the immunoelectrode (for example, the immunoelectrode also can be disposed on different layers of chips) and to the shape of the immunoelectrode; and all of these changes and improvements fall within the protection scope of the present invention. The protection scope of the present invention is defined by the attached claims and the equivalents thereof.

What is claimed is:

1. A method for preparing an immunoelectrode system, comprising the following specific steps:
    (1) forming a conductive polymer layer on a gold-plated base layer to obtain a conductive polymer/gold-plated base layer;
    (2) forming an antibody layer on the conductive polymer layer to obtain an antibody/conductive polymer/gold-plated base layer, wherein the antibody/conductive polymer/gold-plated base layer serves as an immunoelectrode;
    (3) performing porous modification by forming a porous protective layer on a surface of the antibody layer of the antibody/conductive polymer/gold-plated base layer to obtain a porous protective layer/antibody/conductive polymer/gold-plated base layer; and
    (4) fixing a bare gold-plated base layer to an outer side of the porous protective layer/antibody/conductive polymer/gold-plated base layer to obtain the immunoelectrode system,
    wherein, in the step (3), performing the porous modification comprises uniformly mixing a film forming reagent material with a solvent to form a solution, and then dropwise adding the solution to the surface of the antibody layer so as to obtain the porous protective layer on the surface of the antibody layer of the antibody/conductive polymer/gold-plated base layer, wherein the film forming reagent material is selected from the group consisting of polystyrene, polyaniline, tert-butyl polyacrylate, polycarbonate and polyvinyl alcohol, and the solvent is selected from the group consisting of chloroform, tetrahydrofuran, benzene and $CS_2$.

2. The method for preparing an immunoelectrode system according to claim 1, wherein the step (1) includes the following specific steps:
    S11. cleaning the gold-plated base layer after gold plating with ethanol and water, and drying in air for later use; and
    S12. putting the gold-plated base layer in a reaction solution and performing an overnight no-light reaction in a nitrogen atmosphere and under an ice-bath condition, the time of the overnight no-light reaction being 10-16 h, and then rinsing with pure water and blow drying with nitrogen, so as to modify a surface of the gold-plated base layer with the conductive polymer layer, to obtain the conductive polymer/gold-plated base layer.

3. The method for preparing an immunoelectrode system according to claim 1, wherein forming the antibody layer in the step (2) includes the following specific steps:
    S21. dropwise adding an antibody solution to a surface of the conductive polymer/gold-plated base layer obtained in the step (1), and standing at 37° C. and incubating for 1-2 h, and rinsing with a 0.1% Tween-20 solution to obtain the antibody/conductive polymer/gold-plated base layer; and S22. dropwise adding a blocking buffer to a surface of the antibody/conductive polymer/gold-plated base layer, and standing at 37° ° C. for 0.5-1.5 h to block inactive sites for later use.

4. The method for preparing an immunoelectrode system according to claim 3, wherein, in the step (3), a mass fraction of the film forming reagent material in the solvent is 1-20%, dropwise adding the solution occurs under the conditions of 25° C. and a relative humidity of 50-90%, and after the solvent is completely volatilized, the porous protective layer is formed on the surface of the antibody layer of the antibody/conductive polymer/gold-plated base layer.

5. The method for preparing an immunoelectrode system according to claim 3, wherein the base layer of the gold-plated base layer is a flexible layer of polyester (PET), polypropylene (PP), polyethylene (PE), or acrylonitrile butadiene styrene (ABS); in the step S12, a composition of the reaction solution includes ferric chloride, a conductive polymer, and hydrochloric acid, wherein a concentration of the ferric chloride is 0.01-0.5 mol/L, a concentration of the conductive polymer is 0.01-0.5 mol/L, and a concentration of the hydrochloric acid is 0.01-0.5 mol/L; in the step S21, 15 μL of the antibody solution is dropwise added to the surface of the conductive polymer/gold-plated base layer, wherein a concentration the antibody solution is 0.024 mg/ml antibody; in the step S22, the blocking buffer is a 2% BSA blocking buffer; and in the step (4) the bare gold-plated base layer is fixed by using a double-sided adhesive.

6. The method for preparing an immunoelectrode system according to claim 5, wherein, in the step S12, the composition of the reaction solution includes the ferric chloride, the conductive polymer, the hydrochloric acid and sodium dodecyl sulfonate.

7. The method for preparing an immunoelectrode system according to claim 5, further comprising a microfluidic detection chip including a lower-layer chip, a middle-layer chip, and an upper-laver chip cooperating with each other to define a closed micro-flow channel and a plurality of mutually independent chambers; wherein the micro-flow channel and the mutually independent chambers all penetrate through the middle-layer chip; a sample inlet is formed in the upper-layer chip and communicates with the mutually independent chambers through the micro-flow channel; and the microfluidic detection chip further includes a standard electrode and a working electrode, wherein the antibody/conductive polymer/gold-plated base layer is the working electrode and the bare gold-plated base layer is the reference electrode.

8. The method for preparing an immunoelectrode system according to claim 7, wherein the middle-layer chip further comprises a reaction cavity and a waste liquid cavity and a flow channel I having a stop valve site II between the reaction cavity and the waste liquid cavity, and the standard electrode is disposed on the back of the upper-layer chip and the working electrode is disposed on the front of the lower-layer chip so the reaction cavity enables communication between the standard electrode and the working electrode.

9. The method for preparing an immunoelectrode system according to claim 8, wherein the reaction cavity includes a reaction cavity I and a reaction cavity II and a flow channel II having a stop valve site I between the reaction cavity I and the reaction cavity II, and wherein the reaction cavity II enables the communication between the standard electrode and the working electrode.

10. The method for preparing an immunoelectrode system according to claim 9, wherein a sub-flow channel connects the flow channel II to a cleaning solution cavity.

11. The method for preparing an immunoelectrode system according to claim 9, further comprising a matching detection instrument in contact with the standard electrode via an upper-layer communication hole in the upper-layer chip, and wherein the matching detection instrument is in contact with the working electrode via a lower-layer communication hole in the lower-layer chip.

12. The method for preparing an immunoelectrode system according to claim 10, wherein a sub-flow channel I connects the sub-flow channel to a buffer solution cavity.

* * * * *